United States Patent [19]

Dawson

[11] Plant 5,055

[45] May 24, 1983

[54] CITRUS HYBRID TEMPLEO

[76] Inventor: William P. Dawson, 971 Bay Esplanade, Clearwater, Fla. 33515

[21] Appl. No.: 248,342

[22] Filed: Mar. 27, 1981

[51] Int. Cl.[3] ..... A01H 5/00

[52] U.S. Cl. ..... Plt./45

[58] Field of Search ..... Plt./45, 33, 68

*Primary Examiner*—James R. Feyrer

*Attorney, Agent, or Firm*—Duckworth, Allen, Dyer & Pettis

[57] ABSTRACT

A newly found seedling of a fruit bearing citrus plant characterized by the large size, bright distinctive color, pleasant taste, ease of peeling and sectioning, and flattened shape of the fruit.

6 Drawing Figures

BACKGROUND OF THE INVENTION

The invention described herein is a new and distinct hybrid of a fruit bearing citrus plant discovered by me on my cultivated property known as Dawson Groves, Gillet, Manattee County, Fla. The new hybrid was obtained as a newly found seedling.

My attention was first attracted to the newly found seedling when, between two Temple orange trees on my cultivated property identified above this new seedling was found bearing fruit larger and flatter than that of the Temple orange. Although the parentage of the newly found seedling is not positively known, I believe it resulted from a cross between the Orlando tangelo and the Temple orange. The plant shows characteristics of this lineage with significant differences. As stated above, the hybrid was noted and selected as a result of the outstanding characteristics of its fruit. Fruit produced by the hybrid is distinctive in size, color, shape and taste. Marked characteristics of the hybrid fruit are that it is pleasant tasting, peels easily, is brightly colored and is larger and flatter in shape than the supposed parent varieties, which will allow fruit from the new hybrid to be packed and shipped more easily. These features represent a unique combination which differentiates the new hybrid from all other citrus varieties of which I am aware.

Asexual reproduction was performed at Gillet, Manattee County, Fla., by budding with the distinct and characteristic traits stable and perpetuated through successive generations.

As a varietal name for my new seedling, I have chosen Templeo.

BRIEF DESCRIPTION OF THE DRAWINGS

The accompanying photographs show typical specimen fruit obtained from my new and distinct hybrid citrus plant in color as nearly true as it is reasonably possible to make the same in color photographs of this character.

DETAILED DESCRIPTION OF THE PLANT

Figure 1:
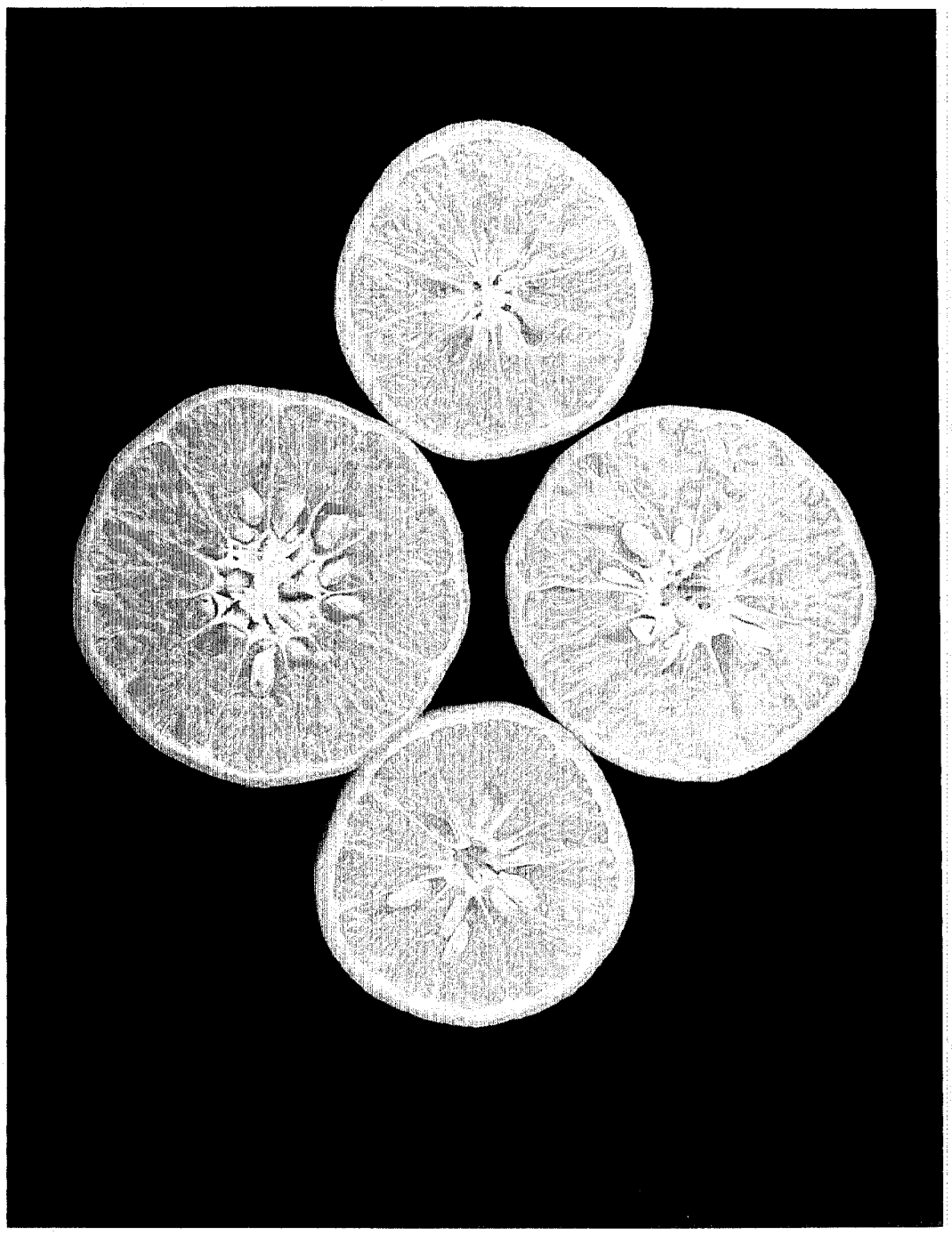
FIG. 1 is a sectional view of the fruit obtained from my hybrid citrus plant.
Figure 2:
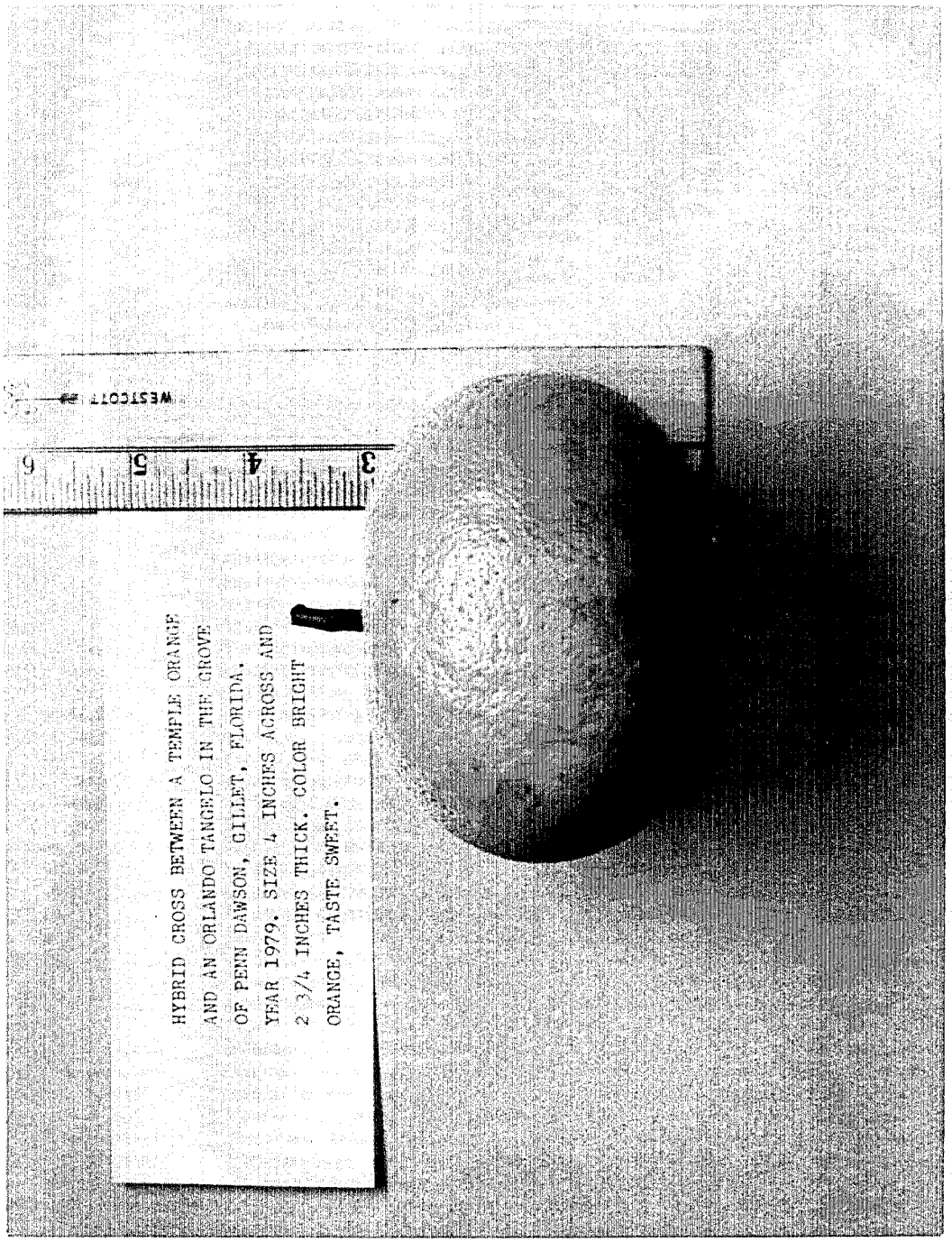
FIG. 2 illustrates the normal size of typical specimen fruit obtained from my new hybrid citrus plant.
Figure 3:
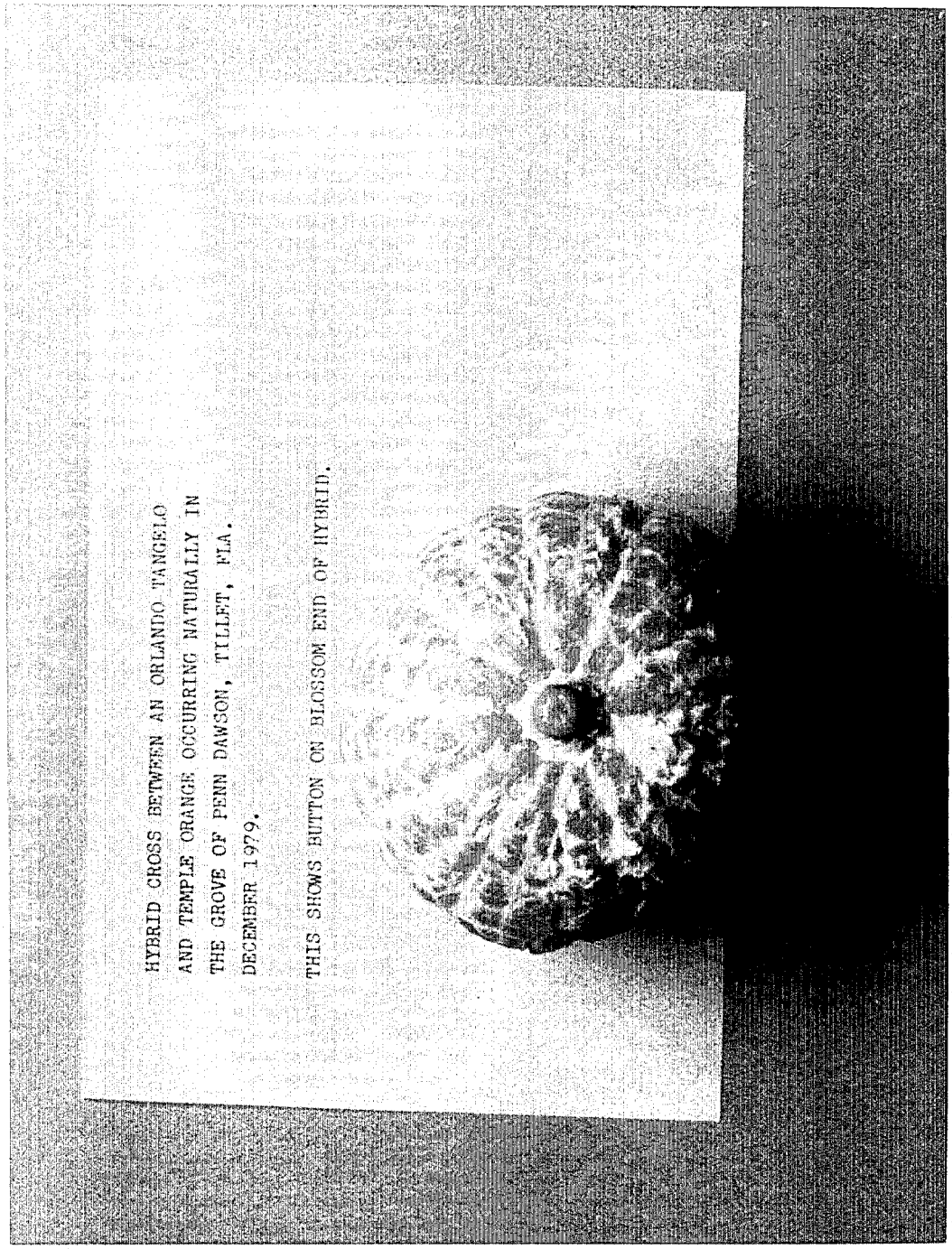
FIG. 3 illustrates a peeled typical specimen fruit obtained from my new hybrid citrus plant.
Figure 4:
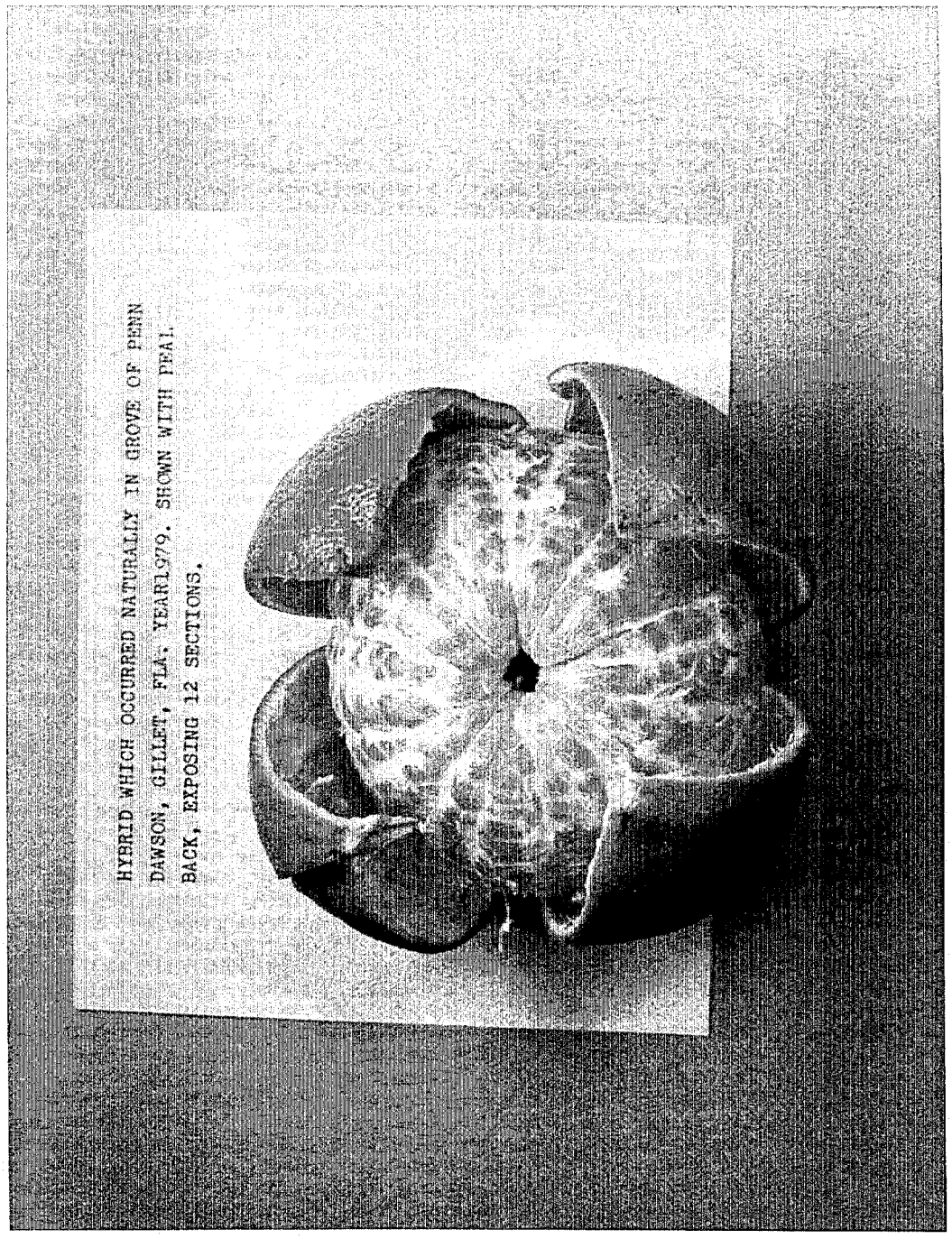
FIG. 4 illustrates a typical specimen fruit obtained from my new hybrid citrus plant with the peel partially removed.
Figure 5:
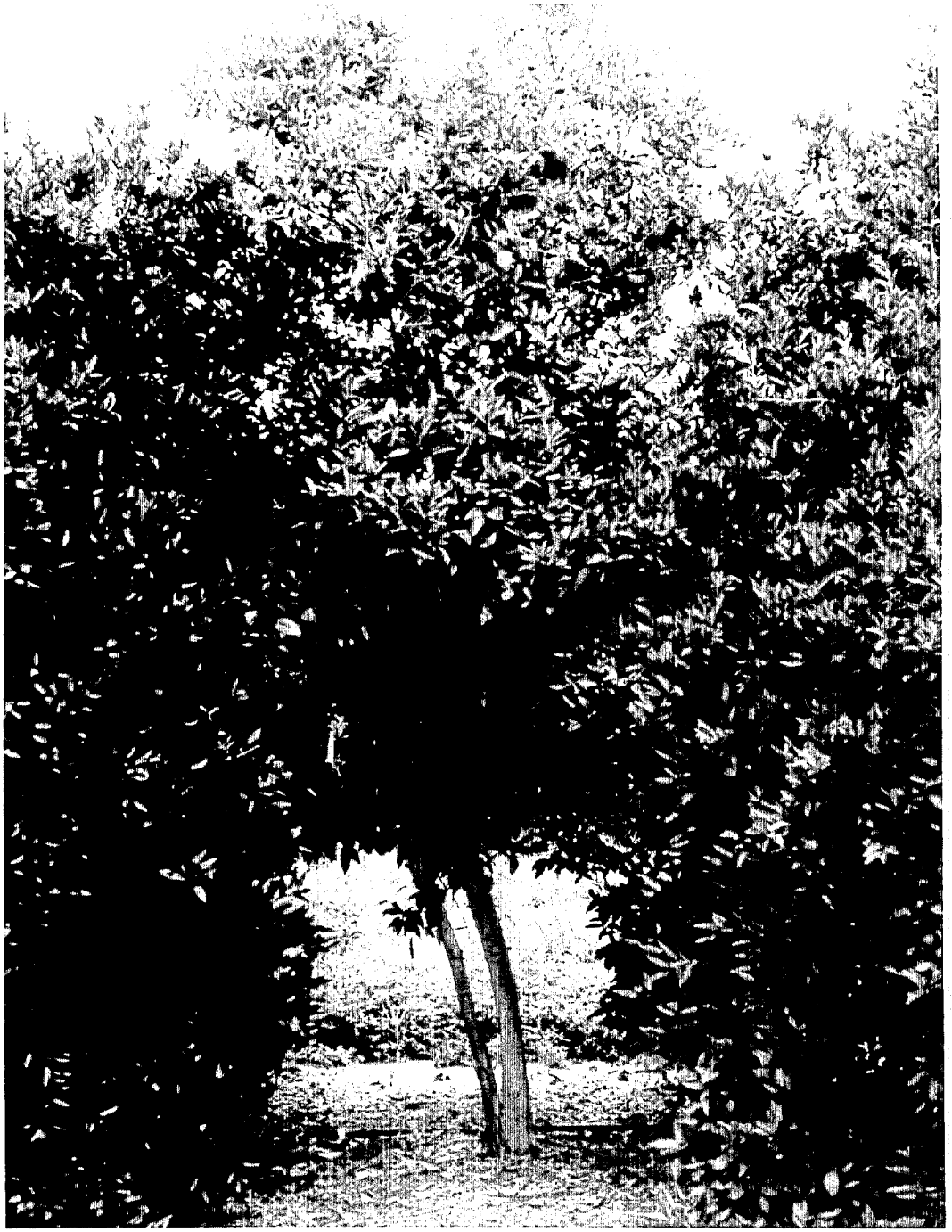
FIG. 5 illustrates one side of a typical specimen of the tree comprising my new hybrid citrus plant.
Figure 6:
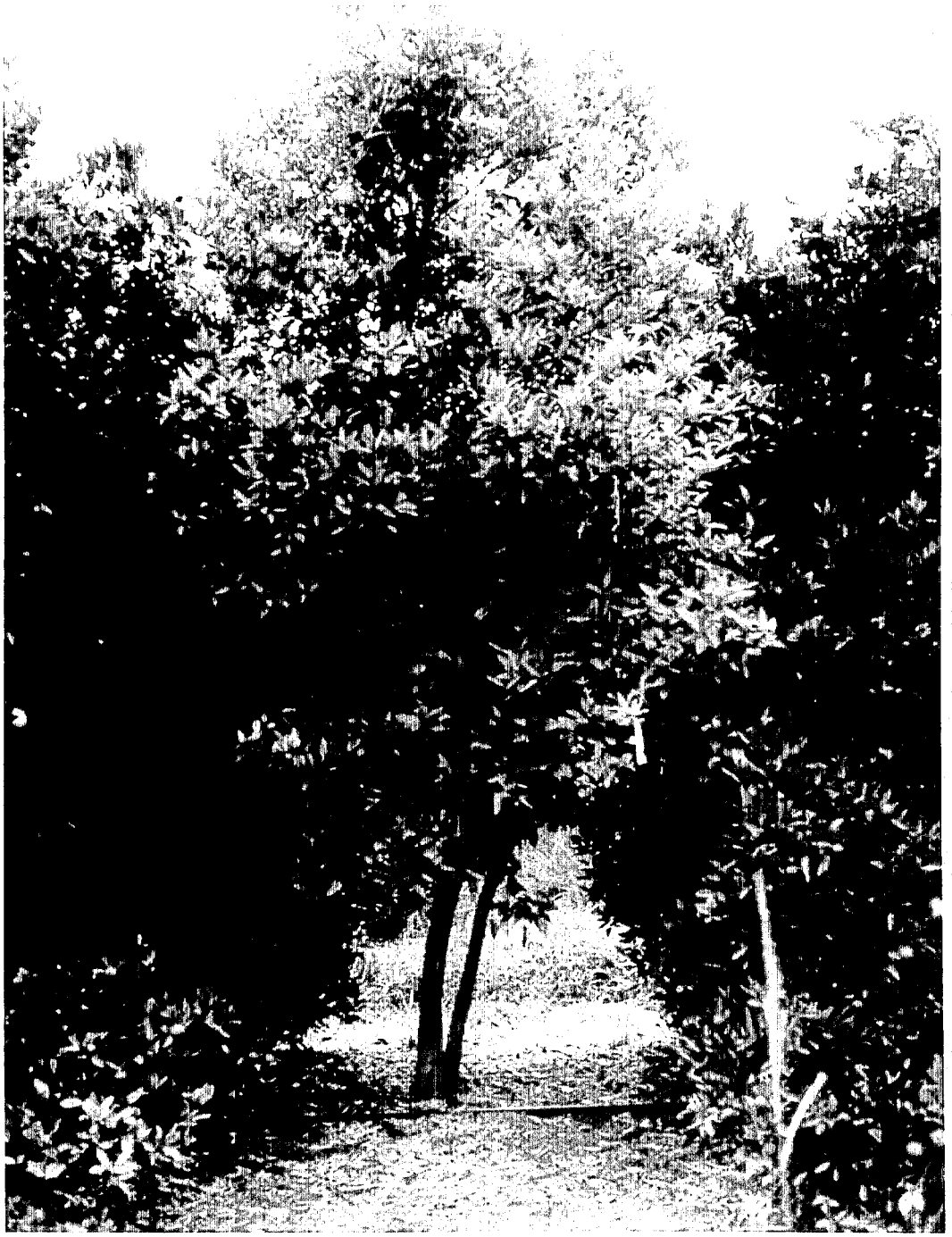
FIG. 6 illustrates the other side of the typical specimen of the tree shown in FIG. 5.

The following is a detailed description of my new hybrid as based on observation of specimen plants at Gillet, Manattee County, Fla. Except where otherwise indicated, color terminology is in accordance with the Universal Color Language and ISCC-NBS Color Name Charts with Centroid Colors distributed by the U.S. National Bureau of Standards.

Parentage: Hybrid believed to be the result of a cross between the Orlando tangelo and the Temple orange.

Propagation: Holds its distinct and characteristic fruit traits through successive propagations by budding.

TREE

Habit: Habit is that of a medium sized tree.

Growth: The newly found seedling has not as yet reached maximum growth. It is anticipated that the tree will attain, depending upon cultural practices, an average of 25–30 feet in height and growth similar to its parentage.

FLOWERS

Flowers are perfect, hypogenous, and fragrant.

Placement: Axillary.

Size: Without pedicel flower averages 15 mm in length. Span (Width) averages 35 mm.

Pedicel: Length averages 7 mm. Possesses greenish-yellow oil glands.

Calyx: Sepals 5; Basally connate; possessing greenish-yellow oil glands. Color 82 yellow. Length averages 3 mm. Span (Width) averages 5 mm.

Corolla: Petals 5; apopetalous; white; possessing greenish-yellow oil glands on abaxial surface. Petals are imbricated, thick, strap-shaped. Petal size averages 16 mm in length, and 5 mm in width.

Gynoecium: Stigma discoid, color 141 green; style deciduous; ovary superior; placentation axile.

Androecium: Stamens number 15 to 30 with the average number 18. Stamens are polyadelphous and inserted on staminal disc with the outer stamens opposite the petals. Filaments are white with anthers 95 deep yellow.

LEAVES

Placement: Alternate.

Shape: Blades unifoliate; narrowly to broadly elliptic; margins crenate; apices acute; basic acute; petiole winged and articulated with leaf blade.

Size: Blade commonly up to 10.5 cm in length and 5.1 cm in width; petiole commonly up to 2.3 cm in length to give total leaf length of 12.8 cm.

Texture: Glabrous; glandular-punctate; medium waxy.

Color of adaxial surface: 125 moderate olive green.

Color of abaxial surface: 117 strong yellow green.

SPINES

Frequency: Frequency of spines on seedling is low. Spines are born singly and in many cases are absent.

Location: Spines are axillary, located at the side of the leaf bud, above the leaf.

Size: Spine size varies with majority of spines either small or large. Few are of intermittent size. Small spines average 5 mm in length, 1 mm width at widest point. Large spines average 20 mm in length and 2 mm in width at widest point.

Shape: Acicular.

Color: 146 Dark Green.

FRUIT

Color: Upper 50% of hesperidium 48 vivid orange; lower 50% of hesperidium 34 vivid reddish orange. (Analysis of fruit color by University of Florida Experiment Station at Lake Alfred, Fla., using Hunter color measurement yields a standard deviation in the a/b ratio of 1.35 plus or minus 0.15.)

Surface: Smooth to finely pitted; glabrous; moderately lustrous.

Shape: Oblate to somewhat sub-globose.

Base: Moderately depressed, narrow to wide ribs restricted to basal area.

Apex: Moderately depressed.

Navel: Small navel sometimes present; approximately 75% of fruit with navel; navel rudimentary with oil cells only, no flesh.

Areole and stylar scar: Disrupted due to presence of navel.

Size: Large; circumference is approximately 27–32 cm; transverse diameter approximately 9.5 cm; axial diameter approximately 7.5 cm; weight approximately 8.5 to 13 ounces.

Calyx: Even; small; lobes equal size; lobes short, bluntly triangular; thin.

Stem: Medium to large.

Rind: Thin to medium; average and median cross-section 2 mm; firm; freely separable; oil glands medium; oil aroma medium, distinctive.

Axis: In median cross-section round, large; hollow; average diameter 2.2 cm.

Segments: Range from 9 extra large to 13 large sized segments; average 12 segments; adherence to rind slight; freely separable; size uniform within fruit; dorsal surface rounded; rag from rind very little; septa thin and tender.

Flesh: Color uniform; 50 strong orange; texture fine and tender; vescicles large, plump.

Juice: Content very abundant; color 68 strong orange yellow (analysis of juice color by University of Florida Experiment Station at Lake Alfred, Fla., reveals a color number of 43.7 on a Huntertab Citrus Colorimeter); brix 10.65% and acid 1.18% to yield 9.0 solids to acid ratio; slight reticulata aroma; overall acidic flavor but with no hint of bitterness; juice has some qualities of the grapefruit, some orange, lemon, lime, but in general has more of citrus fruit flavor and is unlike that of anything on the market now.

Seeds: Many; average of 35–40 per fruit, three per section; sized medium to large; slender to medium; average length 12 mm; average width 6 mm; shape flattened obovoid; surface smooth, weakly veined; color 89 pale yellow; imperfect seeds few.

Season: Early midseason.

The frequency of blooming of my hybrid is once a year, and it is an alternate bearer. Keeping time of fruit on the tree is sixty (60) days after ripening. Fruit keeps well in storage three weeks off of the tree.

Maturation of fruit from this highly productive hybrid peaks from the first week in December to the first week in January, which places it between the peak seasons of the Orlando tangelo and the Temple orange.

In addition, my hybrid has exhibited a marked resistance to cold weather. During the winter of 1981, a specimen of this hybrid, grown on my cultivated property in Gillet, Manattee County, Fla., successfully withstood temperatures below 26° F. for eight hours and below 32° F. for twelve hours with no serious injury to the plant.

It is to be understood that reasonable variations in the characteristics and description of my plant and its fruit may occur when produced under different conditions such as those of climate, soil, stock, fertilizer, location, altitude and other similar factors affecting plant life.

What is claimed is:

1. A new and distinct hybrid of fruit bearing citrus plant substantially as herein described, characterized particularly as to novelty by its fruit exhibiting a large size, bright distinctive color, pleasant taste, ease of peeling and sectioning, and flattened shape.

* * * * *